United States Patent [19]
Asato

[11] 3,993,677
[45] Nov. 23, 1976

[54] 1,2,3,4-TETRAHYDRO-4-OXO-1-NAPHTHYLISOCYANATE

[75] Inventor: Goro Asato, Titusville, N.J.

[73] Assignee: American Cyanamid Company, Stamford, Conn.

[22] Filed: Nov. 3, 1975

[21] Appl. No.: 628,030

[52] U.S. Cl. .............................. 260/453 AR; 71/99; 71/120; 260/454; 260/552 R; 260/553 A; 424/322

[51] Int. Cl.$^2$.............. C07C 119/048; C07C 161/04

[58] Field of Search ........................... 260/453 AR

[56] References Cited
UNITED STATES PATENTS 2,683,160  7/1954  Irwin .................................. 260/453
3,535,322  10/1970  Georgiadis et al. ............. 260/453 X
3,576,812  4/1971  Wiesner et al. .................. 260/453 X Primary Examiner—Lewis Gotts
Assistant Examiner—Dolph H. Torrence
Attorney, Agent, or Firm—Denis A. Polyn

[57] ABSTRACT

This invention relates to 1,2,3,4-tetrahydro-4-oxo-1-naphthylisocyanate and- isothiocyanate and to methods of preparation of said compounds.

The compounds of the present invention are useful as intermediates for the preparation of 1,2,3,4-tetrahydro-4-oxo(oxy)-1-naphthylurea and-thiourea compounds and certain derivatives thereof. The naphthylurea and thiourea compounds are animal growth regulators and herbicides.

3 Claims, No Drawings

1,2,3,4-TETRAHYDRO-4-OXO-1-NAPHTHYLISOCYANATE

BACKGROUND OF THE INVENTION

The resolved 1,2,3,4-tetrahydro-1-naphthylamines have been reported in the literature by R. Weidmann and J. P. Guette, *Comptes Rendus des Seances de l'Academie des Sciences* 268: 2225 (1969) as resulting from the Curtius reactions with the optically active 1,2,3,4-tetrahydronaphthalene-1-carboxylic acid azides. This work establishes the absolute configuration of the (R) and (S) isomers, but does not suggest the 1,2,3,4-tetrahydro-4-oxo-1-naphthylisocyanate or isothiocyanate of the present invention, nor does it suggest the tetrahydro-4-oxo-1-naphthylureas and thioureas derived therefrom, described and claimed in the Application for United States Letters Patent, Ser. No. 582,559 filed May 30, 1975 (Goro Asato inventor); said Application being herein incorporated by reference.

This invention also relates to methods of preparation of the above-identified 1,2,3,4-tetrahydro-4-oxo-1-naphthylisocyanate and isothiocyanate.

SUMMARY OF THE INVENTION

This invention relates to novel compounds of the formula (I):

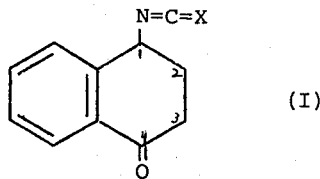

wherein X is oxygen or sulfur.

This invention also relates to the racemic mixtures and to the optically active forms of the compounds identified by formula (I) above. The optically active forms are designated as the (1R) and (1S) isomers, with the (1S) isomers generally being preferred since the tetrahydro-4-oxo-1-naphthylureas and thioureas derived therefrom appear to be biologically more active than the (1R) forms. The preferred (1S) isomers may be illustrated as follows:

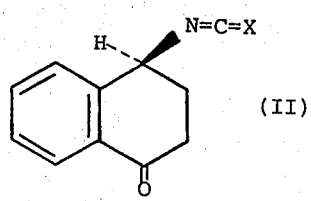

wherein X is as hereinabove defined. The (1R) isomers corresponding to the above (1S) isomers may be illustrated as follows:

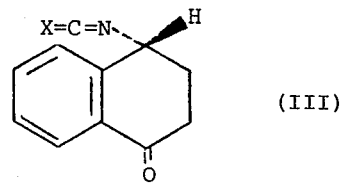

wherein X is as defined for said formula (II) (S) isomer. Hereinafter the terms (R) and (S) will refer to the absolute configuration at the 1-position of the molecule.

The above-identified formulae (II) and (III) optically active isocyanates and isothiocyanates have the same absolute configuration at the 1-position as the 1,2,3,4-tetrahydro-4-oxo-1-naphthylamine used as starting material. In order to obtain the formula (II) (S) isomer or the formula (III) (R) isomer, it is necessary to start with corresponding (S) or (R) isomers of 1,2,3,4-tetrahydro-4-oxo-1-naphthylamine.

DESCRIPTION OF THE INVENTION

In accordance with this invention formula (I) tetrahydro-4-oxo-1-naphthylisocyanate and isothiocyanate, the racemic mixtures or the optically active isomers thereof, can be prepared by the following preferred routes.

A formula (I) isocyanate can be prepared by reacting 1,2,3,4-tetrahydro-4-oxo-1-naphthylamine of formula (IV) or an acid addition salt thereof with phosgene in an anhydrous solvent selected from benzene, toluene, chlorobenzene, chlorinated hydrocarbons or xylene; and if so desired under a blanket of inert gas e.g. nitrogen; at a temperature between 20° C to the boiling point of the solvent selected, until the reaction is essentially complete. The thus obtained formula (I) isocyanate may be used as such for the preparation of the above-identified animal growth regulating urea compounds; or may, if so desired, by recovered from the reaction. The above-described reaction scheme is graphically illustrated below:

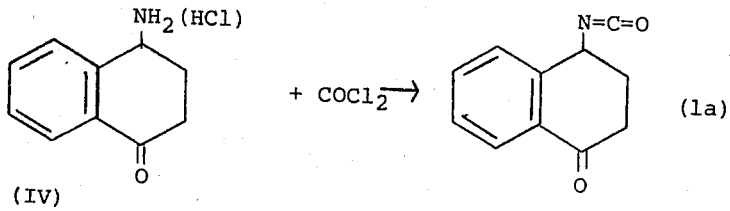

The analogous formula (Ib) isothiocyanates can be prepared by reacting 1,2,3,4-tetrahydro-4-oxo-1-naphthylamine of formula (IV) with equimolar amounts of carbon disulfide, triethylamine and a carbodiimide represented by the formula: G—N=C=N—G, wherein G is cyclohexyl, cycloheptyl, alkyl $C_4$–$C_6$ or the like. This reaction is generally conducted in the presence of an inert solvent such as ethyl acetate, tetrahydrofuran or an ether such as diethyl ether, at a temperature between −10° and +25° C. The product can be isolated and purified by standard laboratory procedures, or may be used without isolation for the preparation of the aforementioned animal growth regulating thiourea compounds. The above reaction can be graphically illustrated as follows:

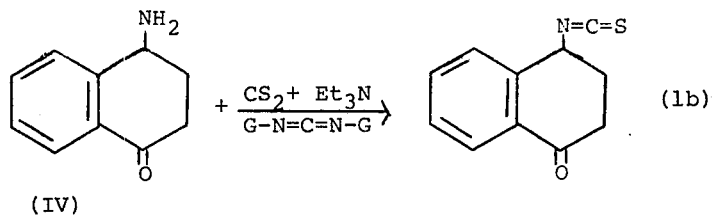

(IV)

wherein G is cyclohexyl, cycloheptyl, alkyl $C_4$–$C_6$, or the like.

The precursor, 1,2,3,4-tetrahydro-4-oxo-1-naphthylamine of formula (IV), common to both of the above-described processes, can be conveniently prepared by the following method.

A racemic mixture of acylated 1,2,3,4-tetrahydro-1-naphthylamine of formula (V) or an optical isomer thereof, is reacted with a 2 to 8 mole equivalent of an oxidizing agent selected from the group consisting of ceric ammonium nitrate, ceric sulfate, chromic anhydride, sodium or potassium bichromate at a temperature between about 0° and 100° C, preferably 20° to 60° C, in a solvent selected from the group consisting of aqueous solutions of acetic acid, acetonitrile, tetrahydrofuran, dioxane, dimethoxyethane, diethylene glycol dimethyl ether, which may contain nitric acid, phosphoric acid or perchloric acid, or chromic anhydride — acetic anhydride, followed by hydrolysis to yield the acid addition salt (e.g. hydrochloride) of 1,2,3,4-tetrahydro-4-oxo-1-naphthylamine as hereinbelow graphically illustrated:

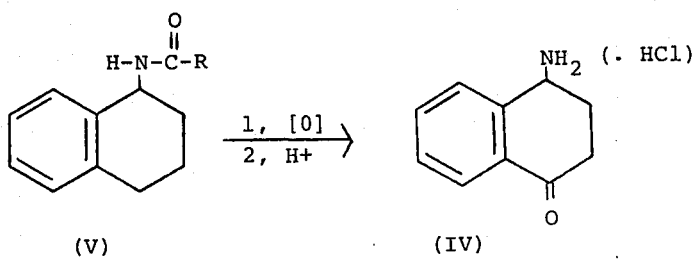

wherein R is H or alkyl $C_1$–$C_4$.

The formulae (Ia) tetrahydro-4-oxo-1-naphthylisocyanate and (Ib) isothiocyanate are obtained as the racemic mixtures by the above described processes. Should the optically active formula (II) (S) or formula (III) (R) isomers be desired, then it is necessary to start with the corresponding optically active (S) or (R) 1,2,3,4-tetrahydro-1-naphthylamine.

A preparation is described hereinbelow whereby the desired optical isomers of said amine can be obtained in high yields.

The racemic mixture of 1,2,3,4-tetrahydro-1-naphthylamine is treated with the appropriate (optically active) N-benzoyl glutamic acid. The (S) - (+) -1,2,3,4-tetrahydro-1-naphthylamine forms a water insoluble salt with (+) -N-benzoyl-(R)-glutamic acid which can be isolated in high yield while the corresponding (R) -(—)amine salt stays in solution. It is not necessary to employ more than one mole of the resolving acid for each two moles of racemic amine, as a cheaper acid, preferably acetic, can be substituted for the balance of required acid. In this way it is possible to obtain a high yield of the desired (S) - (+)-amine based on the resolving acid. The resolved salt, (S)- (+)-1,2,3,4-tetrahydro-1-naphthylamine -(+)-N-benzoyl-(R)-glutamic acid salt, is treated with alkali which liberates the (S)-(+)-amine, separating as an insoluble phase and may be isolated mechanically from the aqueous mixture or extracted with a suitable solvent.

As hereinabove stated, formulae (Ia) 1,2,3,4-tetrahydro-4-oxo-1-naphthyl isocyanate and (Ib) isothiocyanate of the present invention are useful and valuable intermediates for the preparation of 1,2,3,4-tetrahydro-4-oxo-1-naphthylurea and thiourea compounds of formulae (VIa, b and c).

Thus a formula (I) compound may be reacted with an aqueous or alcoholic solution of ammonia, an $R_1$—$NH_2$ or an $$R_1 \diagdown NH$$
$$R_2 \diagup$$

amine to yield the corresponding (thio) urea as hereinbelow graphically illustrated:

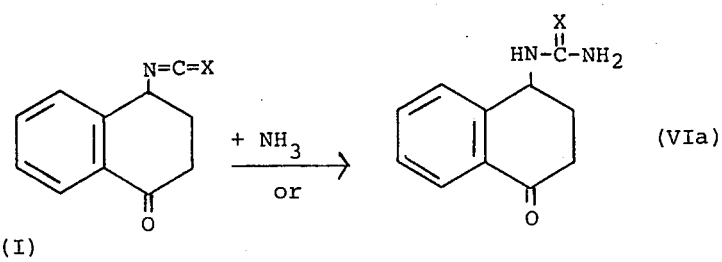

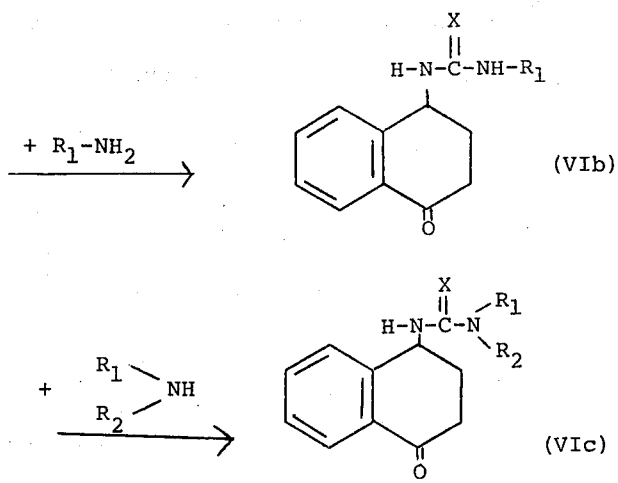

wherein X is oxygen or sulfur; and $R_1$ and $R_2$ represent various preferred substituents.

The formula (VIa, b and c) compounds such as the tetrahydro-4-oxo-1-naphthylurea and thiourea compounds are animal growth promoting agents. As such they can be administered to farm animals (e.g. cattle, sheep) in their diet, implanted in the form of one or more pellets under the skin of the animal or injected subcutaneously or intramuscularly in the form of a solution, suspension or a paste.

When administered in the animal diet, generally about 0.0001% to 0.08% by weight and preferably 0.001% to 0.04% by weight of the drug is effective for increasing weight gain of the animals.

As implants, formula (VI) compounds are formulated to provide a daily drug release of generally about 0.0005 mg to 0.5 mg per kg of body weight and preferably 0.001 mg to 0.2 mg per kg body weight.

The above referred-to feed additives, implants and injectables are prepared by methods known in the art and utilize pharmaceutically acceptable carriers, diluents, solvents and the like.

The following examples are provided by way of illustration and are not intended to limit the invention.

SPECIFIC DISCLOSURE

EXAMPLE 1

Preparation of 1,2,3,4-Tetrahydro-4-oxo-1-naphthyl Isocyanate

A mixture of 1,2,3,4-tetrahydro-4-oxo-1-naphthylamine hydrochloride (24.4 g) and toluene (1000 ml) is heated at reflux to azeotrope water from the mixture. Phosgene is bubbled through the dry refluxing mixture via a capillary tube until virtually no solid remains (5.5 hours). The solution is cooled and nitrogen bubbled through to flush the solution free of excess phosgene. After the purging is completed, the solution is filtered and the filtrate evaporated to dryness in vacuo to afford 19.85 g of the title isocyanate, which has an infrared absorption maximum at 2150 cm$^{-1}$.

Similarly, substitution of 1,2,3,4-tetrahydro-4-oxo-1-naphthylamine for the corresponding amine hydrochloride in the above procedure also yields the title isocyanate.

EXAMPLE 2

Preparation of 1-Methoxy-3-(1,2,3,4-tetrahydro-4-oxo-1-naphthyl-)urea

A mixture of N-methoxyamine (2.5 g), triethylamine (3.04 g) and dry methylene chloride (50 ml) is stirred at room temperature for 20 minutes under a nitrogen atmosphere. Then a solution of 1,2,3,4-tetrahydro-4-oxo-1-naphthyl isocyanate (5.62 g) in dry methylene chloride (50 ml) is added dropwise. After stirring at room temperature for 40 minutes, the reaction mixture is evaporated to dryness in vacuo and the solid residue washed with water (3 × 150 ml) to yield 6.1 g. title product, m.p. 148° to 151° C. Recrystallization from benzene affords crystals, m.p. 155° to 158° C.

EXAMPLE 3

Preparation of 1,2,3,4-Tetrahydro-4-oxo-1-naphthyl isothiocyanate

A solution of 1,2,3,4-tetrahydro-4-oxo-1-naphthylamine (1.74 g) in ethyl acetate (25 ml) is stirred under a nitrogen atmosphere and triethylamine (1.37 ml) is added. The solution is cooled in an ice-bath for 15 minutes and carbon disulfide (0.66 ml) added. A while precipitate forms. The mixture is stirred for 15 minutes at 5° to 10° C and a solution of dicyclohexylcarbodiimide (2.1 g) in ethyl acetate (25 ml) is added dropwise. After stirring overnight, the reaction mixture is filtered and the filtrate evaporated to dryness in vacuo to afford the title isothiocyanate, which has an infrared absorption maximum at 2075 cm$^{-1}$.

EXAMPLE 4

Preparation of 1-Ethyl-3-(1,2,3,4-tetrahydro-4-oxo-1-naphthyl)-2-thiourea

To a solution of 1,2,3,4-tetrahydro-4-oxo-1-naphthyl isothiocyanate (5.0 g) in methylene chloride (100 ml), ethylamine is added via ethanol (15 ml) saturated with ethylamine. After stirring for 18 hours, the mixture is heated at reflux for 2 hours, cooled and evaporated to dryness in vacuo. The residue is triturated with water and the title compound collected and dried; m.p. 134° to 138° C.

Similarly, treatment of the isothiocyanate with alcoholic or aqueous solutions of methylamine and dimethylamine afford 1-methyl- and 1,1-dimethyl-3-(1,2,3,4-tetrahydro-4-oxo-1-naphthyl)-2-thiourea, respectively.

EXAMPLE 5

Preparation of N-Formyl-1,2,3,4-tetrahydro-4-oxo-1-naphthylamine

A solution of 31.4 g of chromic anhydride in 140 ml of acetic anhydride is added dropwise over 80 minutes to a stirred solution of 20 g of N-formyl-1,2,3,4-tetrahydro-1-naphthylamine in 120 ml of acetic anhydride, while maintaining the temperature of the reaction mixture between −8° to 4° C. The reaction mixture is then stirred an additional 35 minutes at 3° C, poured into an ice-water mixture and stirred overnight. The mixture is filtered and 1.5 g of solid collected. The filtrate is saturated with sodium chloride and extracted with 2 × 1000 ml of methylene chloride. The combined organic extracts are washed with 1000 ml of brine and evaporated to dryness in vacuo. The oily residue is triturated with 200 ml of ether to afford a tan solid. The mixture is stirred for awhile and then filtered. The collected tan solid is washed with 2 × 5 ml of ether to afford 13 g of product, m.p. 103°–106° C.

Substitution of sodium or potassium bichromate in acetic acid in the above reaction also affords the title compound.

The title compound is also prepared by reacting N-formyl-1,2,3,4-tetrahydro-1-naphthylamine with four equivalents of ceric sulfate or ceric ammonium nitrate in 50% aqueous acid at room temperature for 10 minutes. The reaction mixture is then filtered, poured into water and extracted with chloroform. The chloroform extract is evaporated to dryness in vacuo to afford the title compound.

Similarly, (+)- and (−)-N-formyl-1,2,3,4-tetrahydro-1-naphthylamines are oxidized by the above procedures to afford (+)- and (−)-N-formyl-1,2,3,4-tetrahydro-4-oxo-1-naphthylamines.

EXAMPLE 6

Preparation of
1,2,3,4-Tetrahydro-4-oxo-1-naphthylamine hydrochloride

A solution of 19.6 g of N-formyl-1,2,3,4-tetrahydro-4-oxo-1-naphthylamine in 214 ml of 95% ethanol and 214 ml of 2N hydrochloric acid is heated at reflux for 3 hours and then stirred at room temperature for 2 days. The solution is filtered and the filtrate concentrated in vacuo to afford a dark residue. The residue is dried using ethanol to remove water in vacuo. This procedure affords 20.2 g of the title compound, m.p. 200° to 216° C (dec.).

EXAMPLE 7

Preparation of
1,2,3,4-Tetrahydro-4-oxo-1-naphthylurea and N-substituted analog thereof A solution of 1,2,3,4-Tetrahydro-4-oxo-1-naphthylisocyanate (5.0 g) in tetrahydrofuran is added to a rapidly stirred aqueous concentrated ammonium hydroxide solution (excess) to afford 1,2,3,4-tetrahydro-4-oxo-1-naphthylurea.

Similarly, substitution of ammonia in the above reaction by methylamine, dimethylamine, propylamine, isopropylamine, ethylamine, diethylamine, dipropylamine, butylamine, 2-butylamine and dibutylamine affords 1-methyl-, 1,1-dimethyl, 1-propyl-, 1-isopropyl-, 1-ethyl-, 1,1-diethyl-, 1,1-dipropyl-, 1-butyl-, 1-(2-butyl)-, and 1,1-dibutyl-3-(1,2,3,4-tetrahydro-4-oxo-1-naphthyl)urea, respectively.

EXAMPLE 8

Mouse Growth Regulant Tests

CFI female mice from Carworth Farm are received when they are 6 weeks old. They are housed 10 to a cage in air-conditioned rooms (72°–76° F) with automatically controlled lights, 14 hours on and 10 hours off. The basal diet used in these studies is Purina Laboratory Chow (see description below), which is supplied ad libitum. Water is also allowed ad libitum.

Thirteen days after arrival, the mice are weighed in groups of 10 and assigned at random to the different treatments. The concentration of the different compounds in the diet is indicated in the following Tables. Twelve days later the mice are weighed again and the experiment terminated. At least three cages (30 mice) of untreated controls are included in each test. Test data is provided in Table I below, wherein data is reported as percent weight gain over controls. The following is a description of the diet to which the growth-promoting compounds are added.

EXAMPLE 9

Preparation of
N-Formyl-1,2,3,4-tetrahydro-4-oxo-1-naphthylamine

A solution of 31.4 g of chromic anhydride in 140 ml of acetic anhydride is added dropwise over 80 minutes to a stirred solution of 20 g of N-formyl-1,2,3,4-tetrahydro-1-naphthylamine in 120 ml of acetic anhydride, while maintaining the temperature of the reaction mixture between −8° C to 4° C. The reaction mixture is then stirred an additional 35 minutes at 3° C, poured into an ice-water mixture and stirred overnight. The mixture is filtered and 1.5 g of solid collected. The filtrate is saturated with sodium chloride and extracted with 2 × 1000 ml of methylene chloride. The combined organic extracts are washed with 1000 ml of brine and evaporated to dryness in vacuo. The oily residue is triturated with 200 ml of ether to afford a tan solid, the mixture stirred for a while and is then filtered. The collected tan solid is washed with 2 × 5 ml of ether to afford 13 g of product, melting point 103°–106° C.

Substitution of sodium or potassium bichromate in the above reaction also affords the title compound.

The title compound is also prepared by reacting N-formyl-1,2,3,4-tetrahydro-1-naphthylamine with four equivalents of ceric sulfate or ceric ammonium nitrate in 50% aqueous acid at room temperature for 10 minutes. The reaction mixture is then filtered, poured into water and extracted with chloroform. The chloroform extract is evaporated to dryness in vacuo to afford the title compound.

Similarly, (+)- and (−)-N-formyl-1,2,3,4-tetrahydro-1-naphthylamines are oxidized by the above procedures to afford (+)- and (−)-N-formyl-1,2,3,4-tetrahydro-4-oxo-1-naphthylamines.

EXAMPLE 10

Preparation of 1,2,3,4-Tetrahydro-4-oxo-1-naphthylamine hydrochloride

A solution of 19.6 g of N-formyl-1,2,3,4-tetrahydro-4-oxo-1-naphthylamine in 214 ml of 95% ethanol and 214 ml of 2N hydrochloric acid is heated at reflux for 3 hours and then stirred at room temperature for 2 days. The solution is filtered and the filtrate concentrated in vacuo to afford a dark residue. The residue is dried using ethanol to remove water in vacuo and this procedure affords 20.2 g of the title compound, melting point 200°–216° C (dec.).

EXAMPLE 11

Preparation of 1,2,3,4-Tetrahydro-4-oxo-1-naphthylisocyanate

A mixture of 1,2,3,4-tetrahydro-4-oxo-1-naphthylamine hydrochloride (19.8 g) and 500 ml of toluene is stirred rapidly at 85° C and phosgene is bubbled into the mixture until a virtually clear solution forms. Nitrogen is passed through the solution, the mixture filtered to remove unreacted amine hydrochloride. The filtrate is evaporated to dryness in vacuo to afford 12.9 g of the title isocyanate.

| DIET | |
|---|---|
| GUARANTEED ANALYSIS | |
| Crude protein not less than | 23.0% |
| Crude fat not less than | 4.5% |
| Crude fiber not more than | 6.0% |
| Ash not more than | 9.0% |
| INGREDIENTS | |
| Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium, phosphate, iodized salt, feric ammonium citrate, iron oxide, manganous oxide, cobalt carbonate, copper oxide, zinc oxide. | |

Table I

Effectiveness of 1,2,3,4-Tetrahydro-4-oxo-naphthylureas as Animal Growth-Promoting Agents Reported as Percent Weight Gain Over Controls Using Mices as the Test Animal

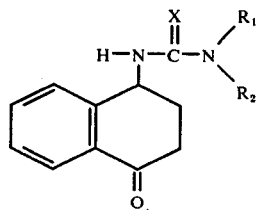

| Rate ppm in Diet | X | $R_1$ | $R_2$ | % Weight Gain Over Controls |
|---|---|---|---|---|
| 50 | O | H | H | 35.71 |
| 100 | | | | 97.40 |
| 200 | | | | 93.51 |
| 200 | O | $CH_3$ | H | 69.00 |
| 400 | O | 2-Bu | H | 19.00 |
| 200 | S | $C_2H_5$ | H | 36.5 |

I claim:
1. A compound of the formula:

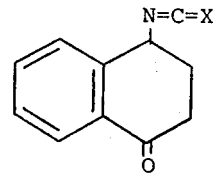

wherein X is oxygen, the racemic mixture and the optical isomers thereof.

2. The racemic mixture according to claim 1, wherein X is oxygen; 1,2,3,4-tetrahydro-4-oxo-1-naphthyl isocyanate.

3. The optical isomers according to claim 1, wherein X is oxygen; 1,2,3,4-tetrahydro-4-oxo-1-napththyl isocyanate.

* * * * *